United States Patent [19]

Tokoro

[11] Patent Number: 5,977,185
[45] Date of Patent: Nov. 2, 1999

[54] METHOD FOR PREVENTION AND TREATMENT OF PRODUCTION DISEASE OF GENETICALLY IMPROVED LIVESTOCK AND POULTRY

[75] Inventor: Toru Tokoro, Tokyo, Japan

[73] Assignee: RTA Associates, Inc., Tokyo, Japan

[21] Appl. No.: 09/132,233

[22] Filed: Aug. 11, 1998

[51] Int. Cl.$^6$ ..................................................... A61K 31/12
[52] U.S. Cl. ................................................................ 514/690
[58] Field of Search ............................................. 514/690

[56] References Cited

FOREIGN PATENT DOCUMENTS

| 6-287136 | 10/1994 | Japan . |
| 7-123928 | 5/1995 | Japan . |
| 918409 | 3/1960 | United Kingdom . |

*Primary Examiner*—James H. Reamer
*Attorney, Agent, or Firm*—Burns, Doane, Swecker & Mathis, LLP

[57] ABSTRACT

A method for preventing or treating a production disease in genetically improved livestock and poultry is provided. This method comprises orally administering to the livestock or poultry quinones such as ubiquinones. Various production diseases can be effectively prevented or treated by this method, especially production diseases caused by stress from heat or cold.

12 Claims, 1 Drawing Sheet

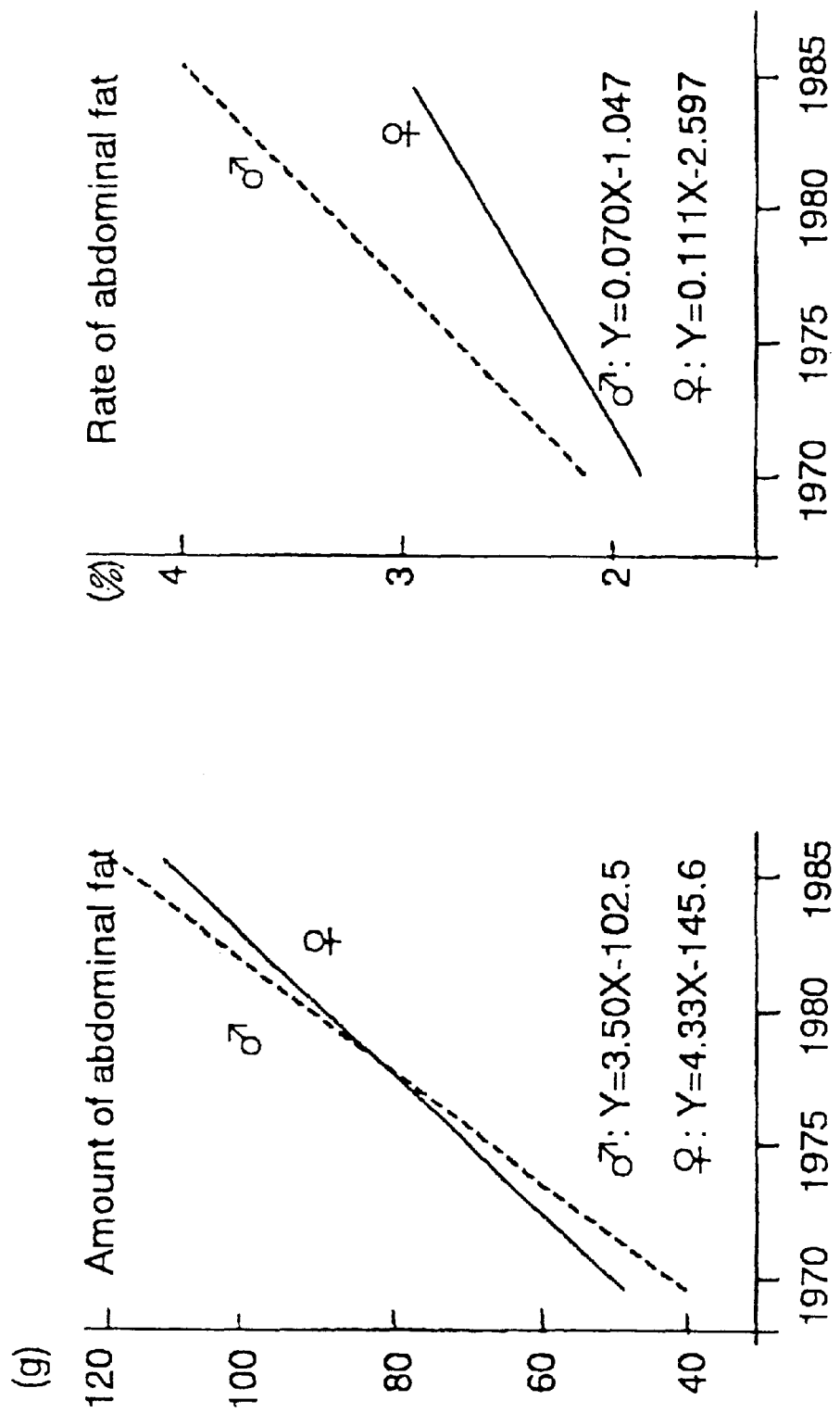

METHOD FOR PREVENTION AND TREATMENT OF PRODUCTION DISEASE OF GENETICALLY IMPROVED LIVESTOCK AND POULTRY

BACKGROUND OF THE INVENTION

The present invention relates to a method for promoting productivity by preventing or treating various production diseases of genetically improved livestock and poultry.

Recently, the livestock and poultry industries have been enhancing genetic improvement of livestock and poultry in body weight, the number of animals bred, the number of eggs laid, the weight and quality of eggs, the amount and quality of milk, the quality of meat, feed conversion ratio (Fc), etc., in order to increase productivity. Also, improvement of feed, sheds, technology for breeding management, sanitary control, etc., have been promoted in order to bring out the genetic potential of the animals being bred. Improvements in feed ingredients and sanitary control are in particularly remarkable. The occurrence of diseases by pathogenic organisms has decreased year by year due to thorough vaccination programs and disinfection.

However, along with such improvements, livestock and poultry have become more susceptible to environmental influences, and so-called production diseases have been increasing every year. It is presumed that genes controlling the productivity of animals and genes controlling disease-resistance and susceptibility to stress, etc. are on the same genetic locus. Therefore, improvement of one characteristic can result in deterioration in the other.

For example, due to development of technology for breeding management in order to promote body-growth, the weight of broilers has been increasing at an annual rate of 6%, and excessive accumulation of fat can be observed (Table 1 and FIG. 1). On the other hand, unexpected negative effects including fatty liver, leg-weakness, sudden death syndrome, heat death in summer, diseases related to disorders of metabolic, circulatory and respiratory systems leading to a decrease of feed intake and weight gain, increase of feed conversion ratio (Fc) in winter, diseases called waterbelly or ascites, and frequent occurrence of respiratory problems have been causing significant economic loss.

TABLE 1

Annual Improvement of Breed in Broilers (10 wks)

| | Body weight (g) | Feed Intake (g) | FC |
|---|---|---|---|
| 1961 | 1,364 | 3,379 | 2.93 |
| 1965 | 1,961 | 4,495 | 2.34 |
| 1968 | 2,180 | 4,879 | 2.28 |
| 1972 | 2,680 | 5,780 | 2.19 |
| 1977 | 2,810 | 5,827 | 2.11 |
| 1983 | 2,920 | 6,048 | 2.10 |

(by Yamane, 1975)

In laying hens, development of technology for breeding management for the purpose of increasing egg production has caused problems such as heat death in summer and decreases in egg production and the quality of eggs. In pigs, breeding for the purpose of increasing body growth (Table 2) and the production of pigs lowered resistance against diseases (pneumonia, diarrhea, etc.) and the quality of meat. Also, in dairy cattle, an increase in milk productivity (Table 3) has resulted in lowered resistance against diseases (mastitis, pneumonia, diarrhea, etc.) and the quality of milk.

In order to prevent such production diseases, measures such as changing the conditions of sheds, sprinkling water, providing more ventilation, and feeding restrictions are taken during the summer. Also, improvement of feed and management technology is being sought. During winter, measures to prevent cold including insulation against wind and cold, heating, etc., and management technology such as feeding restrictions is being sought. Although substances including vitamin C have been considered as a measure against stress from heat or cold, they may not be as effective as expected.

TABLE 2

Annual Improvement of Breed in Pigs

| | Body weight (kg) | Feed Intake (kg) | FC |
|---|---|---|---|
| 1966 | 84.7 | 270.4 | 3.25 |
| 1972 | 92.6 | 282.7 | 3.10 |
| 1981 | 104.8 | 310.2 | 3.00 |
| 1990 | 108.0 | 309.1 | 2.90 |
| 1994 | 108.1 | 304.1 | 2.85 |

TABLE 3

Annual Improvement of Breed in Dairy Cattle

| | Milk Production Yield/head (kg) |
|---|---|
| 1985 | 6,703 |
| 1986 | 6,785 |
| 1987 | 6,979 |
| 1988 | 7,293 |
| 1989 | 7,560 |
| 1999 | 7,568 |

(by Livestock Statistics, 1992)

Japanese Patent Publication No. 6-287136 discloses the use of ubiquinones for preventing ascites in broilers. Japanese Patent Publication No. 7-123928 discloses that coenzyme $Q_9$ or $Q_{10}$ is administered to boilers to prevent ascites and SDS in broilers. However, these publication do not describe or suggest the prevention and treatment of production diseases other than ascites and SDS at low temperatures. Furthermore, the methods described in these publications require long period of administration or large amounts of ubiquinones, which are very expensive. Therefore, these prior art methods are not practical.

SUMMARY OF THE INVENTION

An object of the present invention is to provide a method for preventing or treating production diseases caused by stress from heat or cold in genetically improved livestock and poultry.

Another object of the invention is to provide a method for preventing a decrease in productivity caused by stress from heat or cold in genetically improved livestock and poultry.

Another object of the invention is to provide a method for preventing a deterioration in resistance against infectious diseases, which deterioration is caused by various kinds of stress in genetically improved livestock and poultry.

A further object of the invention is to provide a method for preventing a decrease in egg-productivity caused by stress from heat or cold, and a method for decreasing accumulation of abdominal fat in poultry.

A still further object of the invention is to provide an effective and inexpensive method for preventing production diseases caused by stress from cold in genetically improved poultry.

Other objects and advantages, as well as the nature of the present invention will be apparent from the following description.

In one aspect, the present invention provides a method for preventing or treating production diseases caused by stress from heat or cold in genetically improved livestock and poultry, comprising administering to the livestock or poultry at least one compound selected from quinones having the general formula:

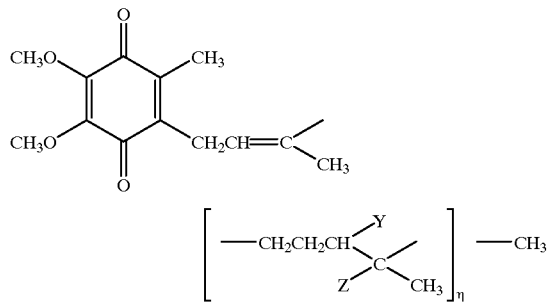

wherein Y and Z independently represent H or $CH_3$, or, taken together, an additional carbon-to-carbon bond, and n is an integer of from 1 to 11.

According to the present method, production diseases can be prevented or treated in genetically improved livestock and poultry, especially at high temperatures or at low temperatures. Specifically, the following conditions can be prevented or treated by the present method: heat death at high temperatures, decreases in productivity at high temperatures or low temperatures, decreases in egg productivity in number and quality in laying hens at high temperatures, accumulation of abdominal fat, and deterioration of resistance against infectious diseases.

The quinones used in the present invention are preferably those in which n is an integer of from 6 to 10 in the above formula. The quinones can be used as a feed additive, and is preferably administered to livestock or poultry in the form of pellets. When the quinones are used along with vitamin E, the amount of quinones to be used in preventing or treating production diseases can be reduced.

In another aspect, the present invention provides a method for preventing production diseases caused by stress from cold in genetically improved poultry, comprising administering to the poultry at least one compound selected from quinones having the general formula:

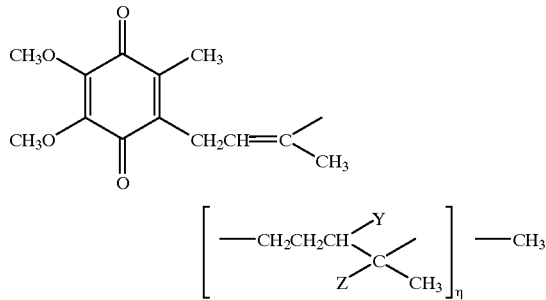

wherein Y and Z independently represent H or $CH_3$, or, taken together, an additional carbon-to-carbon bond, and n is an integer of from 1 to 11, and vitamin E.

The production diseases caused by stress from cold in genetically improved poultry can be effectively prevented by administering the quinones and vitamin E even if the amount of quinones to be administered is much less than in the case in which only quinones are administered. Furthermore, the administration of the quinones for 3 weeks from hatching is enough to prevent production diseases caused by cold in genetically improved poultry.

BRIEF DESCRIPTION OF THE DRAWING

FIG. 1 is a graph showing an annual change of accumulation of abdominal fat in broilers.

DETAILED DESCRIPTION OF THE INVENTION

Quinones used in the present invention have the above general formula, and among theses quinones, those wherein n is an integer of from 6–10 in the formula or mixtures thereof are preferred. Coenzymes Q (ubiquinones), which are quinones in which Y and Z are taken together to represent an additional carbon-to-carbon bond, are more preferred, and in particular coenzyme $Q_9$ (n=8) and coenzyme $Q_{10}$ (n=9) (ubidecarenone) are preferred.

It is generally considered that ubiquinones are coenzymes which participate in the electron transport system in mitochondria, thereby playing an important part in activating cellular respiration and increasing production of ATP conjugatedly and activating respective tissues in an animal body. Due to such a physiological action, ubiquinones are presently used as a therapeutic agent for congestive heart failure in humans. As other medical applications of ubiquinones, ubidecarenone is used for prevention or treatment of convulsions (Japanese Patent Publication No. 1-33082), and prostatic hypertrophy (Japanese Patent Publication No. 63-20804) and as an accelerator of pancreas function (Japanese Patent Publication No. 58-45403).

It is also reported that ubiquinones can be added to a feed as a growth promoting agent for chickens (British Patent No. 918409). However, poultry to be fed with ubiquinones in that patent were not genetically improved poultry. In those days there was no problem of production diseases caused by stress from heat or cold, and therefore the problems to be solved by the present invention did not exist.

Quinones used in the present invention may be prepared by any known method including chemical synthesis, fermentation and extraction from plants. Purified product and crude product obtained by extraction from plants may be used, and microorganism cells containing quinones obtained by fermentation methods may be used as well as purified products.

When quinones of the present invention are used in preventing or treating production diseases, the quinones can be administered to livestock or poultry directly or as a feed additive.

In administering to animals the quinones as a feed additive, the quinones may be mixed with an appropriate excipient, and, if necessary, additives such as vitamins and minerals to make an appropriate form such as a powder, granules or pellets, and then they may be added to a feed, which is administered to animals. Alternatively, a given amount of quinones may be added to a feed, and then may be administered in an appropriate form. However, the quinones are preferably administered to animals in the form pellets, because the quinones are stable when administered in the form of pellets. The quinones are stable with respect to heat, but have problems with light and therefore degraded by light when added to a feed in the form of a powder or granules. The present inventors have found that the quinones are relatively stable with respect to light when administered to animals in the form of pellets. Therefore, it is preferred that the quinones be formed into pellets after mixing with an excipient and, if necessary, any vitamins or minerals, and then added to a feed. Alternatively, the quinones may be added to a feed which may be formed to pellets.

The dosage of the quinones of the present invention is selected according to the kind of animals, age of animals, the purpose of administration, and conditions of symptoms. When the quinones are used as an additive to a feed for preventing production diseases, the concentration of the quinones in the final feed is preferably from about 1 to about 100 mg/kg, and more preferably from 5 to 50 mg/kg.

The period for administration is selected according to the kind of animals, age of animals, the purpose of administration, and conditions of symptoms.

In preventing production diseases caused by stress from cold in genetically improved poultry, the quinones only have to be administered to the poultry during the first 3 weeks of life (from hatching to age 3 weeks). This results in decreasing the amount of the quinones to be administered to poultry because of the small weight of the poultry at this age and a short period of administration. As mentioned above, combination with vitamin E can further decrease the required amount of the quinones.

With respect to Japanese Patent Publication Nos. 6-287136 and 7-123928 as mentioned above, there is no suggestion that when ubiquinones are used along with vitamin E, the amount of ubiquinones to be administered can be decreased remarkably. Also, none of the publications suggests that ubiquinones can be fed only during the first 3 weeks of life of poultry in order to obtain sufficient results in prevention of ascites and SDS.

The following examples are given to further illustrate the present invention. It should be understood that the present invention is not limited to the specific details set forth in the examples.

EXAMPLES

Example 1

This example illustrates the efficacy of quinones in preventing the occurrence of heat death in broiler chickens at high temperatures.

300 remarkably fast-growing male chickens of a bodyweight indicating an age of 35 days were used in each group. This test was performed in summer when the chickens were 35 to 60 days old. The highest temperature recorded inside the shed was 38° C.

Conventional feed (from Itohchu, CP 18.0%, ME 3,230 Kcal) was given to all chickens without restriction. A feed in two experimental groups contained 20 ppm of quinones, and a feed in one experimental group contained 5 ppm of $CoQ_{10}$ and 25 ppm of vitamin E during the latter stage. The obtained results are shown in Table 4.

TABLE 4

| | | Experimental Group | | |
|---|---|---|---|---|
| | Control Group | CoQ6~7 20 ppm | CoQ8~10 20 ppm | CoQ10 + VitE 5 ppm 25 ppm |
| Initial number of chickens | 310 | 303 | 315 | 298 |
| Final number of chickens | 188 | 267 | 284 | 270 |
| Mortality(%) | 39.4 | 11.9 | 9.8 | 9.4 |
| Survival rate(%) | 60.6 | 88.1 | 90.2 | 90.6 |

It can be observed from the above results that the mortality of the experimental groups was less than half of that of the control group, and the survival rates of the experimental groups were higher. Therefore, by administering quinones during a hot summer period, the occurrence of heat death can be decreased, and productivity can be expected to increase.

Example 2

This example illustrates the efficacy of quinones in productivity of broilers at high temperatures.

10 remarkably fast-growing male chickens, aged 33 days, were used in each group. This test was performed for one week. The broilers in 18° C. group were bred in 18° C., and the broilers in 33° C. groups were exposed to heat of 33° C. at Zootron (Environmental Laboratory) for a period of one week.

As a feed, conventional feed (from Itochu, CP 19.0%, ME 3,290 Kcal) for broilers was given without restriction. A feed in one experimental group of 33° C. groups contained 20 ppm of quinones and a feed in the other experimental group of 33° C. groups contained 5 ppm of $CoQ_{10}$ and 25 ppm of vitamin E during the latter stage. Weight gain per day (DG), feed intake, and feed conversion (FC) were observed. The obtained results are shown in Table 5.

TABLE 5

| | | 33° C. Group | | |
|---|---|---|---|---|
| | 18° C. Group | Control | CoQ9~10 20 ppm | CoQ10 + VitE 5 ppm 25 ppm |
| Initial BW(g) | 1,823 | 1,823 | 1,819 | 1,825 |
| Final BW(g) | 2,363 | 2,129 | 2,298 | 2,302 |
| WG(g) | 77 | 44 | 68 | 68 |
| Feed Intake/day(g) | 142 | 117 | 131 | 133 |
| FC | 1.84 | 2.66 | 1.93 | 1.96 |

It can be observed from the above results that decrease of productivity in broilers due to heat can be prevented by adding the quinones to the feed. The combination of a quinone and vitamin E can reduce the amount of the quinone to be added to a feed.

Example 3

This example illustrates the efficacy of quinones in promoting egg production with respect to number and quality in laying chickens at high temperatures.

25 laying White Leghorns of age 274 days were used in each group. This experiment was performed at Zootron, and the sensory temperature was set at 30° C. for three groups and 20° C. for one group during this experiment.

As a feed, conventional feed (CP 18.0%, ME 2,850 Kcal) was used, and a feed in one experimental group contained 20 ppm of quinones (mixture of $CoQ_9$ and $CoQ_{10}$ and a feed in the other experimental group contained 5 ppm of $CoQ_{10}$ and 25 ppm of vitamin E. The feeding was restricted to 120 g per hen per day. The lights were on for 16 hours per day. Hau-unit were measured on the same day when the eggs were laid.

After 30 days, the egg production rate, average egg weight, hau-unit, thickness of egg shells, and feed intake were evaluated. The obtained results are shown in Table 6.

TABLE 6

|  | 20° C. Group | 30° C. Group | | |
|---|---|---|---|---|
|  |  | Control | CoQ 20 ppm | CoQ10 + VitE 5 ppm 25 ppm |
| Egg production rate (%) | 92.6 | 82.5 | 90.1 | 90.6 |
| AV.Egg weight(g) | 63 | 59 | 62 | 62 |
| Hau-unit | 92 | 87 | 90 | 89 |
| Thickness of egg shell(mm) | 0.38 | 0.33 | 0.36 | 0.35 |
| Feed Intake/ day(g) | 118 | 95 | 116 | 115 |

It is evident from the above that due to the influence of high temperatures, the feed intake, egg production rate, egg weight and thickness of egg shell were decreased. However, the above results indicate that the experimental groups, which were administered quinone or quinone and vitamin E, were less influenced by heat and that the quinone was effective in improving egg production rate and quality of eggs at high temperatures.

Example 4

This example illustrates the efficacy of quinones in productivity in fattening pigs at high temperatures.

10 fattening pigs of the same litter of approximately 30 kg in weight were used in each group. This experiment was performed at Zootron, and the sensory temperature was kept at 30° C. during this experiment.

As a feed, conventional feed (from Itohchu, at the early stage: CP 16.0%, TDN78.0%, at the latter stage: CP15.0%, TDN77.0%) was given continuously, and a feed in one experimental group contained 10 ppm of quinones and a feed in the other experimental group contained 5 ppm of $CoQ_{10}$ and 25 ppm of vitamin E.

The obtained results are shown in Table 7.

TABLE 7

|  | Control Group | CoQ10 10 ppm | CoQ10 + VitE 5 ppm 25 ppm |
|---|---|---|---|
| Initial BW(kg) | 30.0 | 30.1 | 29.8 |
| Final BW(kg) | 110.0 | 113.0 | 112.5 |
| BWG(kg) | 80.0 | 82.9 | 82.7 |
| Feed Intake(kg) | 256.0 | 246.2 | 247.0 |
| Fattening Period(day) | 120.0 | 119 | 119 |
| FC | 3.20 | 2.97 | 2.99 |

It can be observed from the above results that the quinones are effective in promoting productivity of fattening pigs when added to a feed during hot weather.

Example 5

This example illustrates the efficacy of quinones in productivity and the prevention of the occurrence of ascites in broilers at low temperatures.

48 remarkably fast-growing male broiler chickens were used in each group. This test was performed when the broilers were 0 days to about 7 weeks old (the time of marketing). The chickens were exposed to cold at a temperature of 5° C. at Zootron for a period of one week from age 14 days to age 21 days.

As a feed, conventional feed (at an early stage: CP 21.0%, ME 3,150 Kcal, at a latter stage: CP18.0%, ME3,270 kcal) was given continuously until the chickens were ready for the market. Experimental groups (Ext.I–V) were given feed containing 5 ppm, 10 ppm or 20 ppm of $CoQ_9$–$CoQ_{10}$, or feed containing 5 ppm of $CoQ_{10}$ and 25 ppm of vitamin E for three weeks from age 0 to 21 days, and no CoQ was added to the feed thereafter until the time for marketing. The obtained results are shown in Table 8.

TABLE 8

|  | CoQ10 Added(ppm) | VitE Added(ppm) | Incidence(%) | |
|---|---|---|---|---|
|  |  |  | Ascites | SDS |
| Control | 0 | 0 | 13.3 | 4.1 |
| Exp.I | 5 | 0 | 10.3 | 5.2 |
| Exp.II | 10 | 0 | 7.3 | 2.1 |
| Exp.III | 20 | 0 | 5.4 | 1.8 |
| Exp.IV | 5 | 25 | 5.27 | 2.0 |
| Exp.V | 20 | 0 | 4.9 | 1.7 |

It can be observed from the above results that the occurrence rates of ascites and SDS were substantially lowered in the experimental groups which were administered quinones. The results also indicate that giving quinones from age 0 to age 21 days can lower the occurrence of ascites and SDS, and that the combination of quinones and vitamin E can reduce the amount of the quinones to be added to a feed.

Example 6

This example illustrates the efficacy of quinones in preventing the accumulation of abdominal fat in broiler chickens.

10,000 remarkably fast-growing male and female broiler chickens were used in each group. This experiment was performed from the end of March to May (from age 0 to 54 days).

As a feed, a conventional feed (from Itohchu, at the early stage: CP 22.0%, ME 3,130 Kcal, at the latter stage: CP18.0%, ME3,230 kcal) was given to chickens without restriction. A feed in experimental groups contained 20 ppm of $CoQ_{10}$ (Experimental Group I) or 5 ppm of $CoQ_{10}$ and 25 ppm of vitamin E (Experimental Group II) during both the early and latter stage. The obtained results are shown in Table 9.

TABLE 9

|  | Exp.I | | Exp.II | | Control | |
|---|---|---|---|---|---|---|
|  | ♂ | ♀ | ♂ | ♀ | ♂ | ♀ |
| Total Meat Yield rate(%) (Breast & Thigh) | 45.06 | 43.69 | 45.01 | 43.03 | 43.68 | 43.15 |
| Percentage of Abdominal Fat(%) | 2.38 | 3.17 | 2.45 | 3.38 | 3.11 | 4.22 |

It is apparent from the above results that total meat yield rate of breasts and thighs in both male and female chickens in the experimental groups was higher than that of the control group. This indicates that by adding quinones to a feed, the meat yield rate can be increased. It can be also seen from the results that the rate of accumulation of abdominal fat in the experimental groups was lower compared with the control group.

Example 7

This example illustrates the efficacy of quinones on productivity of fattening pigs at low temperatures.

10 fattening pigs of the same litter of approximately 30 kg in weight were used in each group. This experiment was performed at Zootron at a sensory temperature of 5° C.

As a feed, a conventional feed (from Itohchu, at the early stage: CP 16.0%, TDN78.0%, at the latter stage: CP15.0%, TDN77.0%) was given continuously, and a feed in experimental groups contained 5 ppm or 10 ppm of quinones.

The obtained results are shown in Table 10.

TABLE 10

|  | Control | Exp.I | Exp.II |
| --- | --- | --- | --- |
| Initial BW(kg) | 30.2 | 30.3 | 30.3 |
| Final BW(kg) | 108 | 110 | 113 |
| FI(kg) | 276 | 265 | 261 |
| Fatting Period(day) | 124 | 122 | 122 |
| DG(g) | 627 | 653 | 678 |
| FC | 3.55 | 3.32 | 3.16 |
| Back Fat Thickness(cm) | 23.2 | 21.8 | 21.2 |

It can be observed from the above results that by adding quinones to a feed for fattening pigs, the productivity of the pigs could be improved in a cold weather.

Example 8

This example illustrates the efficacy of quinones in preventing infectious diseases caused by microorganisms in broiler chickens.

30 remarkably fast-growing broiler chickens were used in each group.

Experimental groups were given a feed containing 5 ppm, 10 ppm or 20 ppm of $CoQ_{10}$, or a feed containing 5 ppm of $CoQ_{10}$ and 50 ppm of vitamin E from the birth. After coliform were administered to chickens intraperitoneally at the age of 3 weeks, observations were made for a period of one week. The obtained results are shown in Table 11.

TABLE 11

| Group | Mortality(%) |
| --- | --- |
| Control Group | 73.3(22/30) |
| Ubidecarenon 5 ppm Group | 53.3(16/30) |
| Ubidecarenon 10 ppm Group | 46.7(14/30) |
| Ubidecarenon 20 ppm Group | 30(9/30) |
| Ubidecarenon 5 ppm Group + Vitamin E 50 ppm Group | 36.7(11/30) |

It can be seen from the above results that the quinones can prevent coliform infections in broiler chickens when added to feed.

I claim:

1. A method for preventing or treating a production disease in genetically improved livestock and poultry, comprising orally administering to the livestock or poultry at least one compound selected from quinones having the general formula:

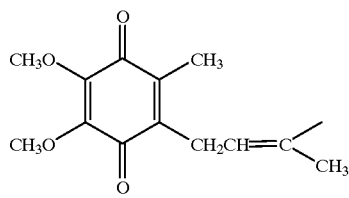

-continued

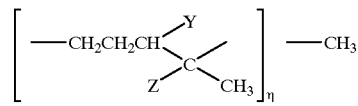

wherein Y and Z independently represent H or $CH_3$, or, taken together, an additional carbon-to-carbon bond, and n is an integer of from 1 to 11.

2. A method according to claim 1, wherein n is an integer of from 6 to 10 in the general formula.

3. A method according to claim 1, wherein the compound is administered as a feed additive.

4. A method according to claim 1, wherein the compound is in the form of pellets.

5. A method according to claim 1, wherein the compound is administered along with vitamin E.

6. A method according to claim 1, wherein the production diseases is caused by stress from heat or cold.

7. A method according to claim 1, wherein the production disease is deterioration of resistance against infectious diseases.

8. A method according to claim 1, wherein the production disease is a decrease of egg production rate in laying hens.

9. A method for preventing a decrease in productivity of genetically improved livestock or poultry at high temperatures or low temperatures, comprising giving to the livestock or poultry at least one compound selected from quinones having the general formula:

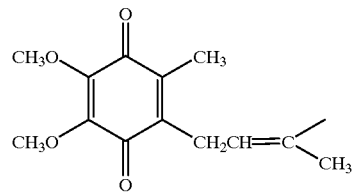

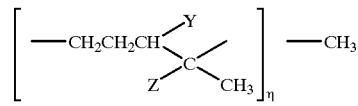

wherein Y and Z independently represent H or $CH_3$, or, taken together, an additional carbon-to-carbon bond, and n is an integer of from 1 to 11.

10. A method for decreasing abdominal fat in genetically improved poultry, comprising giving to the poultry at least one compound selected from quinones having the general formula:

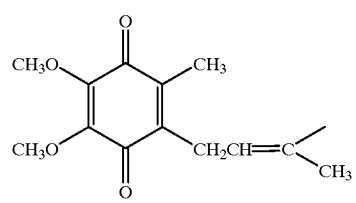

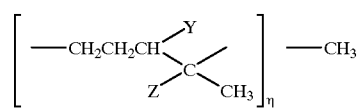

wherein Y and Z independently represent H or $CH_3$, or, taken together, an additional carbon-to-carbon bond, and n is an integer of from 1 to 11.

11. A method for preventing a production disease caused by stress from cold in genetically improved poultry, comprising orally administering to the poultry at least one compound selected from quinones having the general formula:

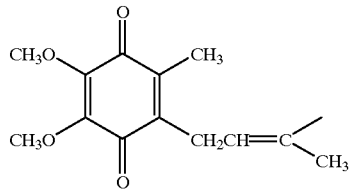

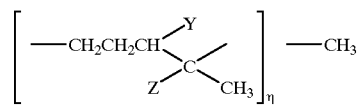

wherein Y and Z independently represent H or $CH_3$, or, taken together, an additional carbon-to-carbon bond, and n is an integer of from 1 to 11, and vitamin E.

12. A method according to claim 11, wherein the administration is carried out for about three weeks from the time of hatch of the poultry.

* * * * *